United States Patent [19]

Burner et al.

[11] Patent Number: 5,362,738

[45] Date of Patent: Nov. 8, 1994

[54] TRICYCLIC PYRIDONE DERIVATIVES

[75] Inventors: Serge Burner, Durmenach-Ferrette, France; Ulrich Widmer, Rheinfelden, Switzerland

[73] Assignee: Hoffmann-La Roche Inc., Nutley, N.J.

[21] Appl. No.: 70,124

[22] Filed: Jun. 1, 1993

Related U.S. Application Data

[62] Division of Ser. No. 889,029, May 26, 1992, Pat. No. 5,258,387, which is a division of Ser. No. 739,757, Aug. 2, 1991, Pat. No. 5,143,912.

Foreign Application Priority Data

Aug. 21, 1990 [CH] Switzerland ............... 2700/90

[51] Int. Cl.$^5$ ................... A61K 31/44; C07D 221/06
[52] U.S. Cl. ........................ 514/294; 546/94
[58] Field of Search ................ 546/80, 94; 514/294

[56] References Cited

U.S. PATENT DOCUMENTS 4,855,297 8/1989 Fischer et al. .................. 514/248

Primary Examiner—Marianne M. Cintins
Assistant Examiner—Phyllis G. Spivack
Attorney, Agent, or Firm—George M. Gould; George W. Johnston; Robert A. Silverman

[57] ABSTRACT

The pyridone derivatives of the formula

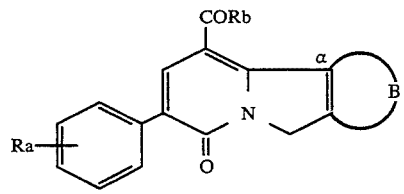

wherein Ra is hydrogen or halogen, Rb is $-OR^1$ or $-NR^2R^3$; $R^1$ is an unsubstituted lower alkyl or a lower alkyl substituted by hydroxy, lower alkoxy, amino, lower alkylamino, di(lower alkyl)amino, di(lower alkyl)carbamoyl or lower alkoxycarbonylamino; $R^2$ is hydrogen or a lower alkyl group which is unsubstituted or substituted by hydroxy, lower alkoxy, amino, lower alkylamino, di(lower alkyl)-amino, di(lower alkyl)carbamoyl or lower alkoxycarbonyl-amino; and $R^3$ is hydrogen or lower alkyl optionally unsubstituted or mono- or disubstituted by lower alkyl, hydroxy, lower alkoxy, lower hydroxyalkyl, lower alkoxyalkyl or phenyl; B and the carbon atom denoted by $\alpha$ taken together is a group of the formula $>C_\alpha-CR^4=CH-CH=CH-$ and $R^4$ is hydrogen, fluorine or chlorine, that can be used for the control or treatment of muscle tension, stress, insomnia, anxiety and/or convulsions.

17 Claims, No Drawings

TRICYCLIC PYRIDONE DERIVATIVES

This is a division, of application Ser. No. 07/889,029 filed May 26, 1992, now U.S. Pat. No. 5,258,387, which is a divisional of Ser. No. 07/739,757 filed Aug. 2, 1991, now U.S. Pat. No. 5,143,912.

SUMMARY OF THE INVENTION

The present invention relates to compounds of the formula

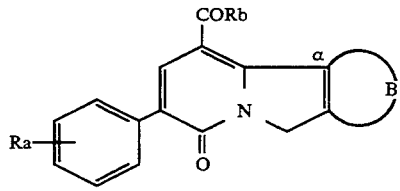

wherein Ra is hydrogen or halogen; Rb is $-OR^1$ or $-NR^2R^3$; $R^1$ is an unsubstituted lower alkyl or a lower alkyl substituted by hydroxy, lower alkoxy, amino, lower alkylamino, di(lower alkyl)amino, di(lower alkyl)carbamoyl or lower alkoxycarbonylamino; $R^2$ is hydrogen, an unsubstituted lower alkyl, or a lower alkyl substituted by hydroxy, lower alkoxy, amino, lower alkylamino, di(lower alkyl)amino, di(lower alkyl)carbamoyl or lower alkoxycarbonylamino; and $R^3$ is hydrogen or lower alkyl; $R^2$ and $R^3$ taken together with the nitrogen atom to which they are attached, is a 1-azetidinyl, 1-pyrrolidinyl, 1-piperidinyl, 4-morpholinyl, 4-thiomorpholinyl or 1-piperazinyl which is unsubstituted or mono- or disub-stituted by lower alkyl, hydroxy, lower alkoxy, lower hydroxyalkyl, lower alkoxyalkyl or phenyl; B and the carbon atom denoted by a taken together is a group of the formula $>C_\alpha$—S—CH=CH— or $>C_\alpha$—$CR^4$=CH—CH=CH— and $R^4$ is hydrogen, fluorine or chlorine,
and pharmaceutically acceptable acid addition salts of compounds of formula I which have at least one basic substituent. The compounds of formula I have muscle relaxant, sedative-hypnotic, anxiolytic and/or anticonvulsive activity and can accordingly be used in the control or prevention of muscle tensions, stress conditions, insomnia, anxiety states and/or convulsions. Accordingly, this invention also is directed to pharmaceutical compositions containing the compounds of formula I and an inert pharmaceutical carrier and to methods of controlling or preventing muscle tension, stress, insomnia, anxiety and convulsions as well as methods for preparing the compounds in formula I and intermediates therefor.

DETAILED DESCRIPTION OF THE INVENTION

The present invention relates to compounds of the formula

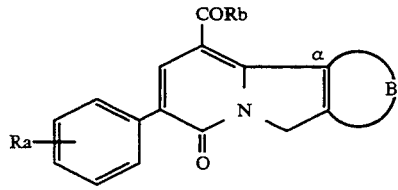

wherein Ra is hydrogen or halogen; Rb is $-OR^1$ or $-NR^2R^3$; $R^1$ is an unsubstituted lower alkyl or a lower alkyl substituted by hydroxy, lower alkoxy, amino, lower alkylamino, di(lower alkyl)amino, di(lower alkyl)carbamoyl or lower alkoxycarbonylamino; $R^2$ is hydrogen, an unsubstituted lower alkyl, or a lower alkyl substituted by hydroxy, lower alkoxy, amino, lower alkylamino, di(lower alkyl)amino, di(lower alkyl)carbamoyl or lower alkoxycarbonylamino; and $R^3$ is hydrogen or lower alkyl; $R^2$ and $R^3$ taken together with the nitrogen atom to which they are attached, is a 1-azetidinyl, 1-pyrrolidinyl, 1-piperidinyl, 4-morpholinyl, 4-thiomorpholinyl or 1-piperazinyl which is unsubstituted or mono- or disub-stituted by lower alkyl, hydroxy, lower alkoxy, lower hydroxyalkyl, lower alkoxyalkyl or phenyl; B and the carbon atom denoted by a taken together is a group of the formula $>C_\alpha$—S—CH=CH— or $>C_\alpha$—$CR^4$=CH—CH=CH— and $R^4$ is hydrogen, fluorine or chlorine,
and pharmaceutically acceptable acid addition salts of compounds of formula I which have at least one basic substituent.

The compounds of formula I have valuable pharmacological properties and can be used for the control or prevention of illnesses. In particular, they have muscle relaxant, sedative-hypnotic, anxiolytic and/or anticonvulsive activity and accordingly are useful in the control or prevention of muscle tensions, stress conditions, insomnia, anxiety states and/or convulsions.

The invention comprises the compounds of formula I including their acid addition salts as well as their use as therapeutically active substances, also processes and intermediates for their preparation and finally pharmaceutical compositions containing the compounds of formula I and an inert pharmaceutical carrier.

As used herein, the term "lower" denotes residues and compounds having a maximum of seven, preferably a maximum of four, carbon atoms. The term "alkyl" alone or micombinantions such as alkoxy, hydroxyalkyl and alkoxyalkyl denotes straight-chain or branched, saturated hydrocarbon residues such as methyl, ethyl, propyl, isopropyl and t-butyl. The term "alkoxy" denotes alkyl groups attached via an oxygen atom, such as methoxy and ethoxy. The term "hydroxyalkyl" denotes alkyl groups substituted by hydroxy, such as hydroxymethyl and 2-hydroxyethyl. The term "halogen" denotes the four forms fluorine, chlorine, bromine and iodine.

The symbol Ra preferably is hydrogen.

In a preferred embodiment the symbol Rb is the group $-OR^1$ and the symbol $R^1$ is lower alkyl.

In a further preferred embodiment the symbol Rb is the group $-NR^2R^3$ and the symbols $R^2$ and $R^3$ each independently are lower alkyl or taken together with the nitrogen atom to which they are attached is a 1-azetidinyl or 1-pyrrolidinyl group which is monosubstituted by lower alkoxy or lower alkoxyalkyl.

The symbol B and the carbon atom denoted by α taken together preferably is a group of the formula $>C_\alpha$—S—CH=CH—, $>C_\alpha$—CH=CH—CH=CH— or $>C_\alpha$—CCl=CH—CH—.

Particularly preferred compounds of formula I are:
N,N-Dimethyl-4,6-dihydro-4-oxo-3-phenyl-pyrido[2,1-a]isoindole-1-carboxamide;
1-[(4,6-dihydro-4-oxo-3-phenylpyrido[2,1-a]isoindol-1-yl)carbonyl]-3-methoxyazetidine;
1-[(4,6-dihydro-6-oxo-7-phenylthieno[2',3':3,4]pyrrolo-[1,2-a]pyridin-9-yl)carbonyl]-3-methoxyazetidine;

(R)-1-[(4,6-dihydro-6-oxo-7-phenylthieno[2',3':3,4-]pyrrolo-[1,2-a]pyridin-9-yl)carbonyl]-2-(methoxymethyl)pyrrolidine;

(S)-1-[(4,6-dihydro-6-oxo-7-phenylthieno[2',3':3,4-]pyrrolo-[1,2-a]pyridin-9-yl)carbonyl]-3-methoxypyrrolidine; and 1-[(10-chloro-4,6-dihydro-4-oxo-3-phenylpyrido[2,1-a]iso-indol-1-yl) carbonyl]-3-methoxyazetidine.

The compounds of formula I and the pharmaceutically acceptable acid addition salts of compounds of formula I which have a basic substituent can be prepared in accordance with the invention by a) reacting in the presence of a condensation agent, a carboxylic acid, or a reactive derivative thereof, of the formula

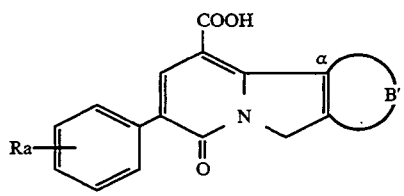

II wherein B' and the carbon atom denoted by α taken together is a group of the formula >$C_α$—S—CH=CH— or >$C_α$—CH=CH—CH=CH— and Ra is hydrogen or halogen, with a compound of the formula $R^1$—OH III or $R^2R^3$NH IV wherein $R^1$, $R^2$ and $R^3$ are as given above for formula I, or b) treating a compound of the formula

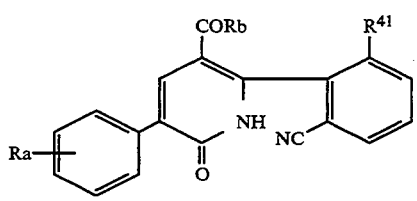

V wherein $R^{41}$ is chlorine or fluorine and Ra and Rb are as given above for formula I,
with zinc in acetic acid, or c) reacting a compound of the formula

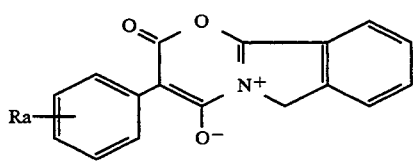

VI wherein Ra is as given above for formula I, with a compound of the formula

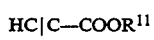 VII wherein $R^{11}$ is lower alkyl, or d) removing the chlorine atom in a compound of the formula

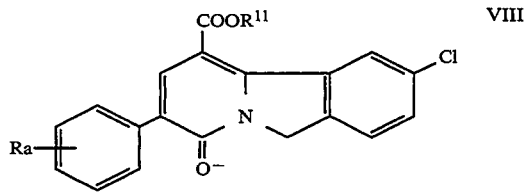

VIII wherein $R^{11}$ and Ra are as given above for formulas VII and I respectively, by hydrogenolysis, or e) cleaving the ether group in a compound of the formula

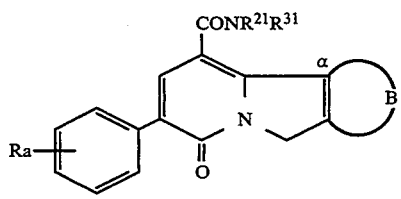

Ia where $R^{21}$ and $R^{31}$ taken together with the nitrogen atom to which they are attached is a 1-azetidinyl, 1-pyrrolidinyl, 1-piperidinyl, 4-morpholinyl, 4-thiomorpholinyl or 1-piperazinyl group which is substituted by lower alkoxy or lower alkoxyalkyl and Ra and B are as given above for formula I, or f) cleaving off the lower alkoxycarbonyl group in a compound of the formula

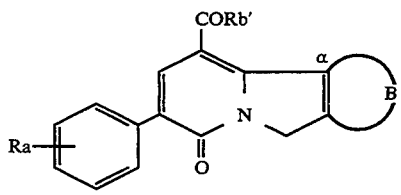

Ib wherein Rb' is the group —$OR^{12}$ or —$NR^{22}R^{32}$, $R^{12}$ and $R^{22}$ each is a lower alkyl group substituted by lower alkoxycarbonylamino and $R^{32}$ is hydrogen or lower alkyl and Ra and B are as given above for formula I, and g) if desired, converting a compound of formula I obtained in the above processes which has at least one basic substituent into a pharmaceutically acceptable acid addition salt.

The compounds of formula I in which B and the carbon atom denoted by α taken together is the group of the formula >$C_α$—S—CH=CH— or >$C_α$—CH=CH—CH=CH— can be prepared in accordance with process variant a). The reaction can be carried out, for example, in the presence of a condensation agent and a base in an inert organic solvent. Suitable condensation agents are, for example, 2-(1H-benzotriazol-1-yl)-1,1,3,3-tetramethyluronium hexafluorophosphate, and 1H-1-benzotriazolyloxy-tris(dimethylamino)-phosphonium hexafluorophosphate. Suitable solvents are, for example, N,N-dimethylformamide and dioxane. Suitable bases are, for example, tertiary amines such as triethylamine, N-methylmorpholine and 4-(dimethylamino)pyridine. The reaction is preferably carried out in a temperature range of room temperature to the reflux temperature of the solvent.

The desired reaction can, however, also be performed by firstly converting the carboxylic acid of formula II into a reactive derivative by conventional means and then reacting the resulting compound with a compound of formula III or IV in the presence of a base. As reactive derivatives there are preferably used the corresponding carboxylic acid chlorides which are conveniently prepared by treatment with thionyl chloride in the presence of a small amount of N,N-dimethylformamide in toluene. Suitable bases are, for example, the aforementioned tertiary amines. The reaction is preferably carried out in a temperature range of about room temperature to the reflux temperature of the reaction mixture, conveniently at room temperature.

The compounds of formula I in which B and the carbon atom denoted by $a$ taken together is a group of the formula >$C_\alpha$—CCl=CH—CH=CH— or >$C_\alpha$—CF=CH—CH=CH— can be prepared in accordance with process variant b). The zinc is preferably used in the form of zinc powder and the reaction is preferably carried out at the reflux temperature of the reaction mixture.

The compounds of formula I in which Rb is the group —OR$^1$, R$^1$ is lower alkyl and B and the carbon atom denoted by $a$ taken together is >$C_\alpha$—CH=CH—CH=CH, can be prepared in accordance with process variant c). The reaction is conveniently carried out at an elevated temperature, preferably above 80° C. Accordingly, an inert solvent which boils at an elevated temperature, preferably above 80° C. is preferably used. Aromatic hydrocarbons such as toluene or xylene are especially suitable solvents, with the reaction being preferably carried out at the reflux temperature.

The compounds of formula I in which Rb is the group —OR$^1$, R$^1$ is lower alkyl and B and the carbon atom denoted by $a$ taken together is >$C_\alpha$—CH=CH—CH=CH— can also be prepared in accordance with process variant d). For the hydrogenolysis, palladium/carbon is preferably used as the catalyst and a lower alkanol such as methanol and ethanol is preferably used as the solvent. It is preferably carried out in the presence of ammonium formate as the hydrogen source and in a temperature range of room temperature up to the reflux temperature of the reaction mixture.

The compounds of formula I in which Rb is the group —NR$^2$R$^3$ and R$^2$ and R$^3$ taken together with the nitrogen atom to which they are attached is a 1-azetidinyl, 1-pyrrolidinyl, 1-piperidinyl, 4-morpholinyl, 4-thiomorpholinyl or 1-piperazinyl group which is substituted by hydroxy or lower hydroxyalkyl can be prepared in accordance with process variant e). This ether cleavage is preferably carried out in an inert organic solvent and in the presence of an alkali metal iodide such as sodium iodide and a tri(lower alkyl)chlorosilane such as trimethylchlorosilane. Acetonitrile is an are especially suitable solvent. The reaction temperature preferably lies in a temperature range of room temperature to the reflux temperature of the reaction mixture, more preferably at the reflux temperature of the reaction mixture.

The compounds of formula I in which Rb is the group —OR$^1$or —NR$^2$R$^3$, R$^1$ and R$^2$ each independently is a lower alkyl group which is substituted by amino, and R$^3$ is hydrogen or lower alkyl can be prepared in accordance with process variant f). This reaction is preferably carried out by treatment with trifluoroacetic acid. The reaction temperature preferably lies in a temperature range of room temperature up to the reflux temperature of the reaction mixture, with the reaction being preferably carried out at room temperature.

The compounds of formula I which have a basic substituent can be converted into pharmaceutically acceptable acid addition salts in accordance with process variant g). There come into consideration not only salts with inorganic acids, but also salts with organic acids. Hydrochlorides, hydrobromides, sulphates, nitrates, citrates, acetates, maleates, succinates, methanesulphonates, p-toluenesulphonates and the like, are examples of such salts. These salts can be manufactured according to conventional methods.

The compounds of formulas II, V, VI and VIII are used as starting materials and can be prepared, for example, in accordance with Reaction Schemes I-VI hereinafter.

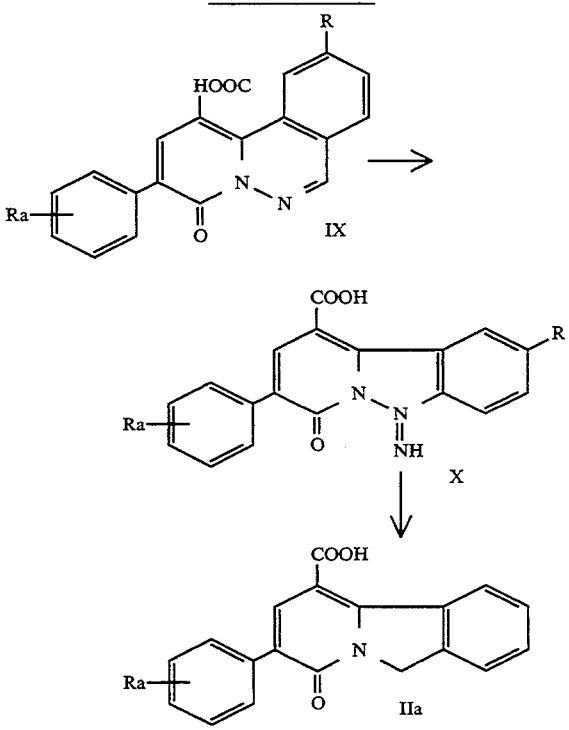

Reaction Scheme I

R is hydrogen or chlorine and Ra is as defined for formula I.

A compound of formula X is obtained by treating a compound of formula IX with an alkali metal hydroxide, e.g. potassium hydroxide, in a lower alkanol such as methanol and ethanol. This reaction is preferably carried out at the reflux temperature of the reaction mixture. The compounds of formula IX belong to a class of compounds described U.S. Pat. No. 4,855,297.

The desired compound of formula IIa, i.e. a compound of formula II in which B and the carbon atom denoted by $a$ taken together is >$C_\alpha$—CH=CH—CH=CH—, is obtained by hyrogenolyzing a compound of formula X. For the hydrogenolysis, palladium/carbon is preferably used as the catalyst, ammonium formate is preferably used as the hydrogen source and a lower alkanol such as methanol and ethanol is preferably used as the solvent. It is preferably carried out in a temperature range of room temperature to the reflux temperature of the reaction mixture.

Reaction Scheme II

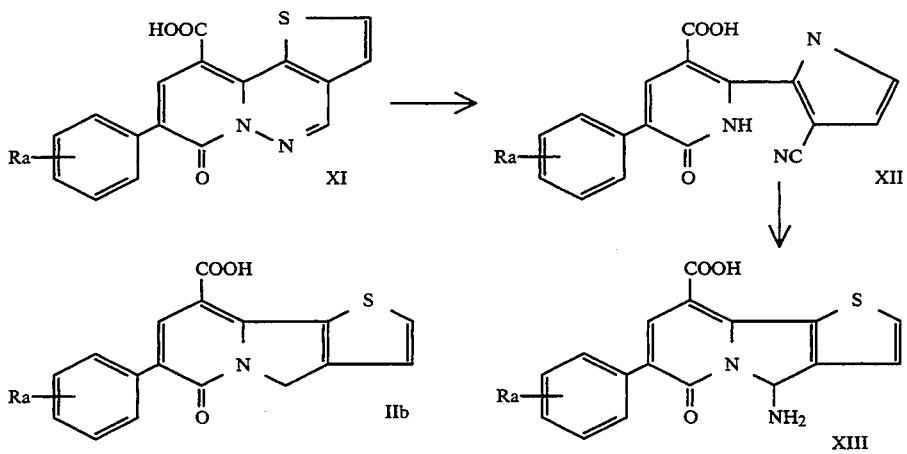

Ra is hydrogen or halogen.

A compound of formula XII is obtained by treating a compound of formula XI with an alkali metal hydroxide, e.g. potassium hydroxide, in a lower alcohol such as methanol and ethanol. This reaction is preferably carried out at the reflux temperature of the reaction mixture. The compounds of formula XI also belong to a class described in U.S. Pat. No. 4,855,297.

A compound of formula XIII is obtained by catalytically hydrogenating a compound of formula XII. For the catalytic hydrogenation palladium/carbon is preferably used as the catalyst and a mixture of a lower alkanol such as methanol and ethanol and an aqueous solution of an alkali metal bicarbonate such as sodium bicarbonate is preferably used as the solvent. The reaction is preferably carried out in a temperature range of room temperature to the reflux temperature of the reaction mixture.

The desired compound of formula IIb, i.e. a compound of formula II in which B and the carbon atom denoted by $\alpha$ taken together is $>C_\alpha$—S—CH=CH—, is obtained by treating a compound of formula XIII with zinc, preferably in the form of zinc powder, in acetic acid, preferably at the reflux temperature of the reaction mixture.

Reaction Scheme III

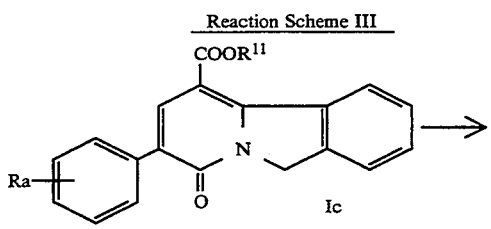

-continued
Reaction Scheme III

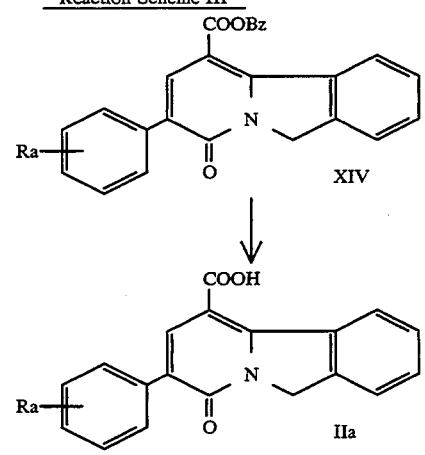

Bz is benzyl, $R^{11}$ is lower alkyl and Ra is hydrogen or halogen.

The compound of formula XIV is obtained by treating a compound of formula Ic with benzyl alcohol in the presence of tetraethyl orthotitanate. Benzyl alcohol is preferably used as the solvent and the treatment is conveniently carried out at an elevated temperature, preferably in a temperature range of about 100° C. to about 150° C.

The desired compound of formula IIa, i.e. a compound of formula II in which B and the carbon atom denoted by $\alpha$ taken together is $>C_\alpha$—CH= CH—CH=CH—, is obtained by hydrogenolyzing a compound of formula XIV. For the hydrogenolysis, palladium/carbon is preferably used as the catalyst, elementary hydrogen is preferably used as the hydrogen source and a lower alkenol such as methanol and ethanol is preferably used as the solvent. It is preferably carried out in a temperature range of room temperature to the reflux temperature of the reaction mixture, but conveniently at room temperature.

Reaction Scheme IV

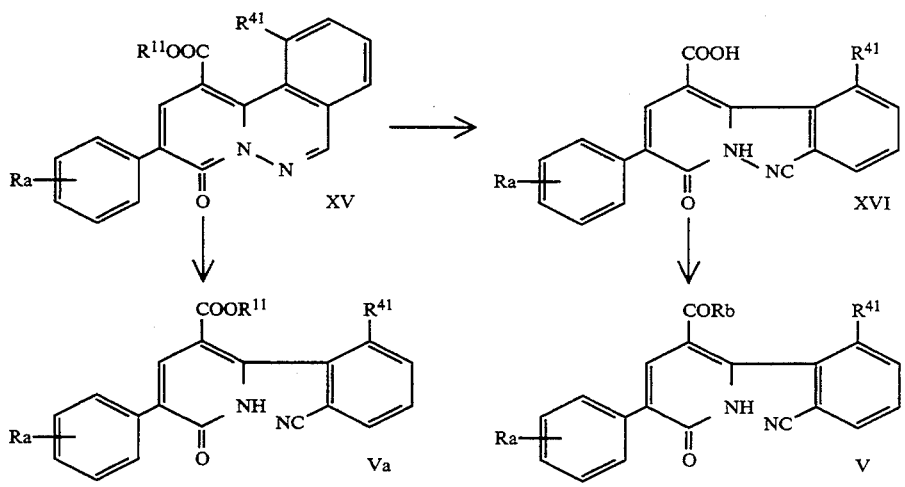

Ra is hydrogen or halogen, $R^{11}$ is lower alkyl and $R^{41}$ is chlorine or fluorine.

A compound of formula XVI is obtained by treating a compound of formula XV with an alkali metal hydroxide, e.g. potassium hydroxide, in a lower alkanol such as methanol and ethanol. This reaction is preferably carried out at the reflux temperature of the reaction mixture.

The carboxylic acid chloride corresponding to the carboxylic acid of formula XVI is obtained by treating a compound of formula XVI with thionyl chloride in the presence of a small amount of N,N-dimethylformamide in toluene. The acid chloride is then reacted with a compound of formula III or IV above in the presence of a base. The desired compound of formula V is thus obtained. Suitable bases are the tertiary amines mentioned above, especially triethylamine. N,N-Dimethylformamide and dioxane are, for example, suitable solvents. The reaction is conveniently carried out at room temperature.

The desired compound of formula Va, i.e. a compound of formula V in which Rb is the group —$OR^1$, and $R^1$ is lower alkyl, is obtained by treating a compound of formula XV with an alkali metal lower alcoholate, preferably an alcoholate corresponding to the residue $R^{11}$, e.g. sodium methylate, in a lower alkanol such as methanol. This reaction is preferably carried out at the reflux temperature of the reaction mixture. The compounds of formula XV belong to a class of compounds described in U.S. Pat. No. 4,855,297.

Reaction Scheme V

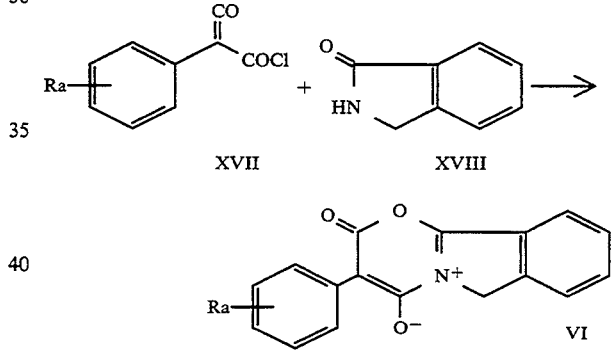

Ra is hydrogen or halogen.

The desired compound of formula VI is obtained by reacting a compound of formula XVII with a compound of formula XVIII in an inert solvent and in a temperature range of about −10° C. to about room temperature. An aromatic hydrocarbon such as benzene or toluene is preferably used as the solvent. The reaction is preferably carried out between about 0° C. and 5° C.

Reaction Scheme VI

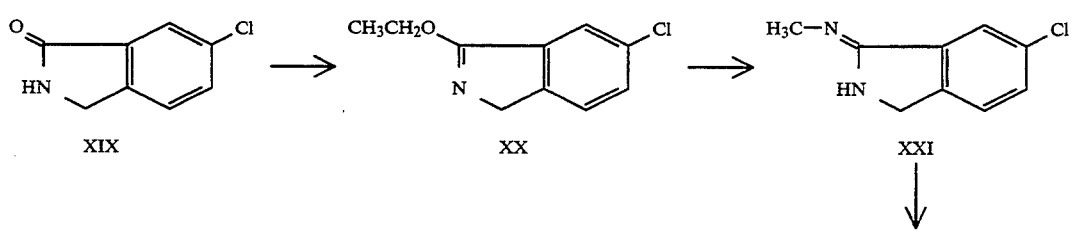

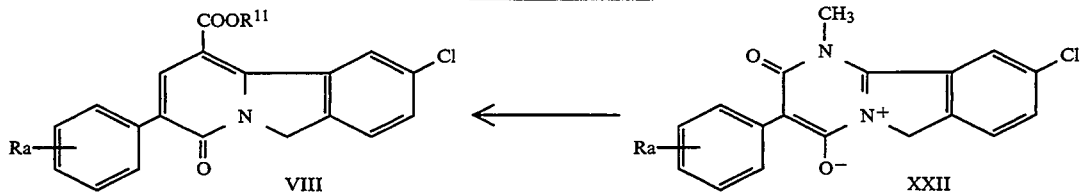

Ra is hydrogen or halogen and $R^{11}$ is lower alkyl.

A compound of formula XX is obtained by treating a compound of formula XIX with triethyloxonium tetrafluoroborate. A chlorinated lower hydrocarbon such as methylene chloride is preferably used as the solvent and the treatment is conveniently carried out at room temperature.

By treating the compound of formula XX with methylamine hydrochloride there is obtained the hydrochloride of the compound of formula XXI, which can be converted with a suitable base, e.g. sodium hydroxide, into the compound of formula XXI. A lower alkanol such as methanol or ethanol is preferably used as the solvent and the reaction is conveniently carried out at the reflux temperature of the reaction mixture.

A compound of formula XXII is obtained by reacting a compound of formula XVII above with a compound of formula XXI in an inert solvent, and in a temperature range of about −10° C. to about room temperature. An aromatic hydrocarbon such as benzene or toluene is preferably used as the solvent. The reaction is preferably carried out at between about 0° C. and 5° C.

The desired compound of formula VIII is obtained by reacting a compound of formula XXII with a compound of formula VII above. The reaction is conveniently carried out at an elevated temperature, preferably above 80° C. An inert solvent which boils at an elevated temperature, preferably above 80° C., is therefore preferably used. Aromatic hydrocarbons such as toluene or xylene or the like are especially suitable solvents, with the reaction being preferably carried out at the reflux temperature.

The compounds of formulae II, V, VI, VIII, X, XII, XIII, XIV, XVI and XXII which are used as intermediates are novel and are part of the present invention. The remaining compounds which are used as starting materials or intermediates belong to classes of known compounds.

As mentioned above, the compounds of formula I have valuable pharmacological properties. In particular, they display pronounced muscle relaxant, sedative-hypnotic, anticonvulsive and/or anxiolytic properties and have a low toxicity. These properties can be demonstrated, for example, in the antipentetrazole test which is described below and which is generally recognized for recording such properties.

In this animal experiment the compound under investigation is administered orally to mice and 30 minutes later there are administered intraperitoneally 120 mg/kg of pentetrazole, which causes emprosthotonus and tonic stretchings of the fore and/or hind limbs in unprotected animals 1–4 minutes after the injection. 10 experimental animals are used per dosage of test substance. After counting the protected experimental animals the $ED_{50}$ is determined according to the Probit method. The $ED_{50}$ is that dosage which protects 50% of the experimental animals from the spasmodic seizures caused by pentetrazole. The results which have been obtained with representative members of the class of compound defined by formula I in the experiment described previously are compiled in the following Table. Moreover, the Table contains data concerning the acute toxicity ($LD_{50}$) of some of these compounds in mg/kg in the case of single oral administration to mice.

TABLE

| Compound of formula I in which | | | $ED_{50}$ in mg/kg p.o. | $LD_{50}$ in mg/kg p.o. |
|---|---|---|---|---|
| Ra | Rb | B | | |
| H | Me₂N— | —CH=CH—CH=CH— | 0.73 | 375 |
| " | 3-MeO-azetidino | " | 0.39 | — |
| " | " | —S—CH=CH— | 2.1 | 2500 |
| " | (R)-2-MeOCH₂—Py— | " | 0.76 | 625 |
| " | 3-MeO-pyrrolidino | " | 1.7 | 375 |
| " | 3-MeO-azetidino | —CCl=CH—CH=CH— | 2.2 | — |
| " | (R)-2-MeOCH₂—Py— | —CH=CH—CH=CH— | 2.3 | 1500 |
| " | 4-Me-piperazino | " | 5.7 | 312 |
| " | Morpholino | —S—CH=CH— | 1.32 | 5000 |

Me = Methyl
Py = Pyrrolidino

The compounds of formula I and the pharmaceutically acceptable acid addition salts of compounds of formula I which have a basic substituent can be used as medicaments, e.g. in the form of pharmaceutical preparations. The pharmaceutical preparations can be administered orally, e.g. in the form of tablets, coated tablets, dragées, hard and soft gelatin capsules, solutions, emulsions or suspension. However, the administration can also be carried out rectally, e.g. in the form of suppositories, or parenterally, e.g. in the form of injection solutions.

For the preparation of pharmaceutical preparations the compounds of formula I of the invention can be processed with pharmaceutically inert, inorganic or organic carriers. Lactose, maize starch or derivatives thereof, talc, stearic acid or its salts and the like can be used, for example, as such carriers for tablets, coated tablets, dragées and hard gelatin capsules. Suitable carriers for soft gelatin capsules are, for example, vegetable oils, waxes, fats, semi-solid and liquid polyols and the like. Depending on the nature of the active substance no carriers are, however, generally required in the case of soft gelatin capsules. Suitable carriers for the preparation of solutions and syrups are, for example, water, polyols, saccharose, invert sugar, glucose and the like. Suitable carriers for injection solutions are, for example, water, alcohols, polyols, glycerin, vegetable oils and the like. Suitable carriers for suppositories are, for example, natural or hardened oils, waxes, fats, semi-liquid or liquid polyols and the like.

The pharmaceutical preparations can also contain preserving agents, solubilizing agents, stabilizing agents, wetting agents, emulsifying agents, sweetening agents, coloring agents, flavoring agents, salts for varying the osmotic pressure, buffers, coating agents or antioxidants. They can also contain still other therapeutically valuable substances. Medicaments containing a compound of formula I of the invention and a therapeutically inert carrier as well as a process for their manufacture, which comprises bringing a compound of formula I of the invention and, if desired, one or more other therapeutically valuable substances into a galenical form for administration are part of the present invention.

As mentioned above, the compounds of formula I of the invention can be used in the control or prevention of illnesses, especially in the control of convulsions and anxiety states. They can be used in dosage forms as described above having muscle relaxant, sedative-hypnotic, anticonvulsive and/or anxiolytic properties. The dosage can vary within wide limits and will, of course, be fitted to the individual requirements in each particular case by the attending clinician. In the case of oral administration the daily dosage lies in a range of about 1 mg to about 100 mg.

The following Examples illustrate the present invention. However, the Examples are not intended to limit the invention in any manner. All temperatures are given in degrees Celsius. The Examples were carried out as written unless otherwise indicated.

EXAMPLE 1

A suspension of 2.9 g of 2,6-dihydro-4-hydroxy-2-oxo-3-phenyl[1,3]oxazino[3,2-a]isoindol-5-ium hydroxide (internal salt) in 100 ml of toluene was treated with 4.2 ml of methyl propiolate under argon and the reaction mixture was heated to boiling under reflux for 25 hours. It was then left to cool and the solvent was removed in a vacuum. The crystalline crude product was chromatographed on silica gel with methylene chloride and then recrystallized from ethyl acetate. There was obtained 0.86 g of methyl 4,6-dihydro-4-oxo-3-phenyl-4H-pyrido[2,1-a]isoindole- 1-carboxylate as white crystals with a m.p. of 206°–207°.

The 2,6-dihydro-4-hydroxy-2-oxo-3-phenyl[1,3]oxazino-[3,2-a]isoindol-5-ium hydroxide (internal salt) used as the starting material was prepared as follows:

A solution of 1.81 g of ct-carbonyl-phenylacetyl chloride in 20 ml of benzene was cooled in an ice bath under argon. After the addition of 1.33 g of 2,3-dihydro-1H-isoindol-1-one the cooling bath was removed and the brown suspension was stirred for a further 30 minutes. The solvent was evaporated in a vacuum. There was obtained 2.9 g of 2,6-dihydro-4-hydroxy-2-oxo-3-phenyl[1,3]-oxazino[3,2-a]isoindol-5-ium hydroxide (internal salt) as yellow-brown crystals.

EXAMPLE 2 a) A suspension of 1.29 g of 4,6-dihydro-4-oxo-3-phenylpyrido[2,1-a]isoindole-1-carboxylic acid in 45 ml of toluene was treated with 0.2 ml of N,N-dimethylformamide and 1.85 ml of thionyl chloride and then stirred at room temperature for 16 hours. The solvent was removed in a vacuum and the residue was taken up in 40 ml of dioxane. 1.78 ml of triethylamine and a solution of 0.41 g of 3-methoxyazetidine in 3 ml of dioxane was then added thereto in succession, whereupon the mixture was stirred at 25° for 30 minutes. After removing the solvent in a vacuum the residue was dissolved in 100 ml of methylene chloride. This solution was washed with 5 percent sodium hydrogen carbonate solution and water, dried over sodium sulphate, filtered and evaporated. By chromatography on silica gel with methylene chloride/diethyl ether (9:1) and methylene chloride/acetone (9:1) and recrystallization from ethanol there was obtained 1.26 g of 1-[(4,6-dihydro-4-oxo-3-phenylpyrido[2,1-a]isoindol-1-yl)carbon-yl]-3-methoxyazetidine as slightly yellowish crystals with a m.p. of 174°.

In an analogous manner:

b) Using dimethylamine there was obtained N,N-dimethyl-4,6-dihydro-4-oxo-3-phenylpyrido[2,1-a]isoindole-1-carboxamide with a m.p. of 207°–209° (ethanol).

c) Using N-methyl-N-(2-methoxyethyl)amine there was obtained after chromatography on silica gel with diethyl ether/toluene (2:1) N-ethyl-4,6-dihydro-N-(2-methoxyethyl)-4-oxo-3-phenylpyrido[2,1-a]isoindole-1-carboxamide with a m.p. of 139°–140° (ethyl acetate).

d) Using (R)-2-(methoxymethyl)pyrrolidine there was obtained after chromatography on silica gel with methylene chloride/diethyl ether (9:1 and 2:1) (R)-1-[[4,6-dihydro-4-oxo-3-phenylpyrido[2,1-a]isoindol-1-yl]carbonyl]-2-( methoxymethyl)pyrrolidine with a m.p. of 130°–131° (ethyl acetate).

e) Using 2-hydroxy-N,N-dimethylacetamide there was obtained after chromatography on silica gel with methylene chloride/diethyl ether (9:1) and methylene chloride/acetone (9:1) (dimethylcarbamoyl)methyl 4,6-dihydro-4-oxo-3-phenylpyrido[2,1-a]isoindole-1-carboxylate with a m.p. of 177°–179° (acetonitrile).

The 4,6-dihydro-4-oxo-3-phenyl-pyrido[2,1-a]isoindole-1-carboxylic acid used as the starting material was prepared as follows:

A. A solution of 1.62 g of tetraethyl orthotitanate in 71 ml of benzyl alcohol was treated with 4.52 g of methyl 4,6-dihydro-4-oxo-3-phenylpyrido[2,1-a]isoindole-1-carboxylate and stirred at 115°–120° under argon for 3 hours. The reaction mixture was then cooled, stirred with 71 ml of 1N hydrochloric acid for 1 hour, diluted with 350 ml of water and extracted several times with methylene chloride. The organic phases were washed with saturated sodium hydrogen carbonate solution, dried over sodium sulphate, filtered and evaporated. The residue was stirred in 710 ml of diethyl ether for 1 hour, suction filtered and the material obtained was dried in a vacuum. There was obtained 4.02 g of benzyl 4,6-dihydro-4-oxo-3-phenylpyrido[2,1-a]isoindole-1-carboxylate as yellowish crystals with a m.p. of 229°.

B. A suspension of 3.88 g of benzyl 4,6-dihydro-4-oxo-3-phenylpyrido[2,1-a]isoindole-1-carboxylate in 140 ml of ethanol was treated with 0.78 g of 10 percent palladium/carbon, whereupon the mixture was hydrogenated for 16 hours. The reaction mixture was diluted with 1,400 ml of water and treated with 4.18 g of sodium carbonate. The catalyst was filtered off and the filtrate was acidified with 25 percent hydrochloric acid. The separated crystals were filtered off under suction, washed with water and dried in a vacuum. There was obtained 2.85 g of 4,6-dihydro-4-oxo-3-phenyl-pyrido[2,1-a]isoindole-1-carboxylic acid as white crystals with a m.p. of 295° (decomposition).

EXAMPLE 3 a) A suspension of 2.0 g of 4,6-dihydro-4-oxo-3-phenylpyrido[2,1-a]isoindole-1-carboxylic acid in 25 ml of N,N-dimethylformamide was treated under argon with 0.91 ml of cis-2,6-dimethylmorpholine and then with 0.81 ml of N-methylmorpholine and 2.8 g of 2-(1H-benzotriazol-1-yl)-1,1,3,3-tetramethyluronium hexafluorophosphate and stirred at room temperature for a further 4.5 hours. The reaction mixture was then poured into a mixture of 50 ml of saturated sodium hydrogen carbonate solution and 250 ml of water. The crystallized-out crude product was filtered under suction and dried. After chromatography on silica gel with toluene and toluene/acetone (9:1) recrystallization was carried out twice from ethyl acetate. There was obtained 1.19 g of cis-4-[(4,6-dihydro-4-oxo-3-phenylpyrido-[2,1-a]isoindol-1-yl)carbonyl]-2,6-dimethylmorpholine as yellow crystals with a m.p. of 226°–228°.

In an analogous manner:

b) Using morpholine there was obtained 4-[(4,6-dihydro-4-oxo-3-phenylpyrido[2,1-a]isoindol-1-yl)carbonyl]morpholine with a m.p. of 262°–266° (acetonitrile).

c) Using diethylamine there was obtained N,N-diethyl-4,6-dihydro-4-oxo-3-phenylpyrido[2,1-a]isoindole-1-carboxamide with a m.p. of 170°–172° (ethyl acetate).

d) Using 3-hydroxyazetidine there was obtained 1-[(4,6-dihydro-4-oxo-3-phenylpyrido[2,1-a]isoindol-1-yl)carbonyl]-3-azetidinol with a m.p. of 238°–242° (methanol).

e) Using 1-phenylpiperazine there was obtained 1-[(4,6-dihydro-4-oxo-3-phenylpyrido[2,1-a]isoindol-1-yl)carbonyl]-4-phenyl-piperazine with a m.p. of 208°–210° (acetonitrile).

f) Using 1-methylpiperazine there was obtained after subsequent treatment with ethereal hydrochloric acid 1-[(4,6-dihydro-4-oxo-3-phenylpyrido[2,1-a]isoindol-1-yl)carbonyl]-4-methyl-piperazine hydrochloride with a m.p. of >300° (methanol).

g) Using tert.-butyl 2-aminoethyl-carbamate there was obtained tert.-butyl [2-(4,6-dihydro-4-oxo-3-phenylpyrido[2,1-a]iso-indole-1-carboxamido)ethyl]-carbamate with a m.p. of 238°–240° (methanol/N,N-dimethylformamide).

h) Using thiomorpholine there was obtained 4-[(4,6-dihydro-4-oxo-3-phenylpyrido[2,1-a]isoindol-1-yl)carbonyl]tetrahydro-2H-1,4-thiazine with a m.p. of 266°–268° (methanol/N,N-dimethylformamide).

i) Using ammonia there was obtained 4,6-dihydro-4-oxo-3-phenylpyrido[2,1-a]isoindole-1-carboxamide with a m.p. of 294°–296° (methanol/N,N-dimethylformamide).

The 4,6-dihydro-4-oxo-3-phenylpyrido[2,1-a]isoindole-1-carboxylic acid used as the starting material was prepared as follows:

A. 3.5 g of 10-chloro-4-oxo-3-phenyl-4H-pyrido[2,1-a]-phthalazine-1-carboxylic acid were added to a solution of 5.6 g of potassium hydroxide in 60 ml of methanol, whereupon the mixture was heated to boiling under reflux for 25 hours. The solvent was then removed in a vacuum and the residue was taken up in 60 ml of water. The product was precipitated by the addition of 2N hydrochloric acid. The crystals were filtered off under suction, washed with water and dried in a vacuum.

There was obtained 3.32 g of 9-chloro-6-imino-4-oxo-3-phenyl-6H-pyrido[2,1-a]isoindole-1-carboxylic acid as yellowish crystals with a m.p. of 266°–268° (decomposition).

B. A suspension of 18.1 g of 9-chloro-6-imino-4-oxo-3-phenyl-6H-pyrido[2,1-a]isoindole-1-carboxylic acid and 18 g of 10 percent palladium/carbon in 900 ml of methanol was treated with 16.3 g of ammonium formate and then heated to boiling under reflux for 90 minutes. The treatment with ammonium formate and subsequent heating were repeated once, whereupon the catalyst was filtered off, the solvent was removed in a vacuum and the residue was taken up in 150 ml of water. The mixture was acidified with 1N hydrochloric acid, the crystals were filtered off under suction and washed with water. There were obtained 12.55 g of 4,6-dihydro-4-oxo-3-phenylpyrido[2,1-a]isoindole-1-carboxylic acid with a m.p. of 277°–278° (decomposition).

This compound was also prepared in an analogous manner starting from 4-oxo-3-phenyl-4H-pyrido[2,1-a]phthalazine-1-carboxylic acid:

There was obtained firstly 6-imino-4-oxo-3-phenyl-6H-pyrido[2,1-a]isoindole-1-carboxylic acid with a m.p. of 240°–245° (decomposition) and therefrom 4,6-dihydro-4-oxo-3-phenylpyrido[2,1-a]isoindole-1-carboxylic acid with a m.p. of 276°–278° (decomposition).

EXAMPLE 4 a) In analogy to Example 2a), from 2.2 g of 4,6-dihydro-6-oxo-7-phenylthieno[2',3':3,4]pyrrolo[1,2-a]pyridine-9-carboxylic acid and diethylamine there was obtained 1.17 g of 4,6-dihydro-N,N-diethyl-6-oxo-7-phenylthieno[2',3':3,4]pyrrolo[1,2-a]pyridine-9-carboxamide with a m.p. of 182°–183° (toluene).

In analogous manner:

b) Using morpholine there was obtained 4-[(4,6-dihydro-6-oxo-7-phenylthieno[2',3':3,4]pyrrolo[1,2-a]pyridin-9-yl)carbonyl]-morpholine with a m.p. of 225°–227° (toluene).

c) Using 3-methoxyazetidine there was obtained 1-[(4,6-dihydro-6-oxo-7-phenylthieno[2',3':3,4 ]pyrrolo[1,2-a]pyridin-9-yl)-carbonyl]-3-methoxyazetidine with a m.p. of 192°–193° (toluene).

d) Using (R)-2-(methoxymethyl)pyrrolidine there was obtained (R)-1-[(4,6-dihydro-6-oxo-7-phenylthieno[2',3':3,4]pyrrolo[1,2-a]pyridin-9-yl)carbonyl]-2-(methoxymethyl)pyrrolidine with a m.p. of 150°–152° (toluene).

e) Using dimethylamine there was obtained 4,6-dihydro-N,N-dimethyl-6-oxo-7-phenylthieno[2',3':3,4]pyrrolo[1,2-c]pyridine-9-carboxamide with a m.p. of 174°–176° (toluene).

f) Using 3-azetidinol there was obtained 1-[(4,6-dihydro-6-oxo-7-phenylthieno[2',3':3,4]pyrrolo[1,2-c]pyridin-9-yl)carbonyl]-3-azetidinol with a m.p. of 269°–271° (N,N-dimethylformamide).

g) Using (S)-2-(methoxymethyl)pyrrolidine there was obtained (S)-1-[[4,6-dihydro-6-oxo-7-phenylthieno[2',3':3,4]pyrrolo[1,2-a]pyridin-9-yl]carbonyl]-2-(methoxymethyl)pyrrolidine with a m.p. of 149°–150° (toluene).

h) Using (S)-3-methoxypyrrolidine there was obtained (S)-1-[(4,6-dihydro-6-oxo-7-phenyl-thieno[2',3':3,4]pyrrolo[1,2-a]-pyridin-9-yl) carbonyl]-3-methoxypyrrolidine with a m.p. of 159°–162° (toluene).

The 4,6-dihydro-6-oxo-7-phenylthieno[2',3':3,4]pyrrolo[1,2-a]pyridine-9-carboxylic acid used as the starting material was prepared as follows:

A. 48.7 g of 7-oxo-8-phenyl-7H-pyrido[1,2-b]thieno[2,3-d]-pyridazine-10-carboxylic acid were added to a methanolic potassium hydroxide solution (prepared from 72 g of potassium hydroxide and 640 ml of methanol) and the mixture was heated to boiling under reflux for about 24 hours. The reaction mixture wass evaporated to half in a vacuum, treated with 80 ml of water and adjusted to pH 1 by the addition of 1N hydrochloric acid. The separated crystals were filtered off under suction, washed with water and dried in a vacuum. There was obtained 48.6 g of 2-(3-cyano-2-thienyl)-1, 6-dihydro-6-oxo-5-phenylnicotinic acid as yellow crystals with a m.p. of 255°–257° (methanol/N,N-dimethylformamide).

B. A suspension of 45.4 g of 2-(3-cyano-2-thienyl)-1,6-dihydro-6-oxo-5-phenylnicotinic acid in 850 ml of methanol was treated with a solution of 59.2 g of sodium hydrogen carbonate in 280 ml of water, whereupon the mixture was stirred for 45 minutes. 2.27 g of 10 percent palladium/carbon were then added thereto and the mixture was hydrogenated at room temperature. After completion of the reaction the mixture was acidified with 400 ml of 2N hydrochloric acid, the catalyst was filtered off and the filtrate was concentrated in a vacuum. After the addition of 400 ml of water, crystals separate. After stirring overnight, the mixture was suction filtered and the yellow crystals were dried. There was obtained in quantitative yield 45.9 g of 4-amino-4,6-dihydro-6-oxo-7-phenylthieno[2',3':3,4]pyrrolo[1,2-a]pyridine-9-carboxylic acid with a m.p. of 227°–235°.

C. A suspension of 45.7 g of 4-amino-4,6-dihydro-6-oxo-7-phenylthieno[2',3':3,4]pyrrolo[1,2-a]pyridine-9-carboxylic acid in 915 ml of acetic acid was treated with 27.6 g of zinc powder and heated to boiling under reflux for 2 hours. The suspension was then cooled and poured into 3,000 ml of water. The excess zinc was for the most part removed by decantation. The separated crystals were filtered off under suction and dried in a vacuum. There was obtained 42.4 g of 4,6-dihydro-6-oxo-7-phenylthieno[2',3':3,4]-pyrrolo[1,2-a]pyridine-9-carboxylic acid with a m.p. of >300° (purity 85–90%). This material was purified further by recrystallization from methanol/N,N-dimethylformamide.

EXAMPLE 5

A suspension of 9.0 g of 4,6-dihydro-4-oxo-3-phenylpyrido[2,1-a]isoindole-1-carboxylic acid in 240 ml of dioxane was treated in succession with 6.7 ml of 2-(dimethylamino)ethanol, 15.7 g of 1H-1-benzotriazolyloxy-tris(dimethylamino)phosphonium hexafluorophosphate and 263 mg of 4-dimethylaminopyridine, whereupon the mixture was heated to boiling under reflux for 80 minutes under argon, treated with 1.58 g of 1-benzotriazolyloxy-tris(dimethylamino)phosphonium hexafluorophosphate and heated for a further 1 hour. The mixture was then left to cool and the separated crystals were filtered off under suction. After stirring with 890 ml of methylene chloride, 475 ml of water and 70 ml of saturated sodium hydrogen carbonate solution for 90 minutes the organic phase was separated and evaporated. The residue was dissolved in 100 ml of methanol, whereupon the solution was acidified with ethereal hydrochloric acid, filtered and the product was precipitated by cooling in an ice bath. There was obtained 2.9 g of 2-(dimethylamino)ethyl 4,6dihydro-4-oxo-3-phenylpyrido[2,1-a]isoindole-1-carboxylate as yellowish crystals with a m.p. of 225°–228°.

EXAMPLE 6

A suspension of 0.9 g of tert.-butyl [2-(4,6-dihydro-4-oxo-3-phenylpyrido[2,1-a]isoindole-1-carboxamido)ethyl]carbamate in 1.6 ml of trifluoroacetic acid was stirred at room temperature. The reaction was finished after about 15 minutes and the reaction mixture was treated slowly with 36 ml of 0.25N sodium hydroxide solution, whereby the product crystallized out. The product was stirred for a short time and then filtered off under suction. After chromatography on silica gel with methylene chloride/methanol (9:1 and 2:1) and recrystallization from methanol there was obtained 0.31 g of N-(2-aminoethyl)-4,5-dihydro-4-oxo-3-phenyl-pyrido[2,1-a]isoindole-1-carboxamide with a m.p. of 216°–218°.

EXAMPLE 7 a) A suspension of 1.85 g of (R)-1-[[4,6-dihydro-6-oxo-7-phenylthieno[2',3':3,4]pyrrolo[1,2-a]pyridin-9-yl]carbonyl]-2-methoxymethyl)pyrrolidine in 20 ml of acetonitrile was treated with 2.74 g of sodium iodide under argon, whereupon the mixture was heated to boiling under reflux and 2.3 ml of trimethylchlorosilane were added dropwise thereto within 25 minutes. The reaction mixture was held at the reflux temperature for 45 minutes and then poured into a solution prepared from 10 ml of 0.1N sodium thiosulphate solution and 70 ml of water. The yellow crystals were filtered off under suction, chromatographed on silica gel with methylene chloride, methylene chloride/diethyl ether (9:1), methylene chloride/acetone (9:1) and methylene. chloride-/acetone (4:1) and then recrystallized from methanol. There was obtained 0.67 g of d(R)-1-[[4,6-dihydro-6-oxo-7-phenylthieno-[ 2',3':3,4]pyrrolo[1,2-a ]pyridin-9-yl ]carbonyl]-2-pyrrolidine-methanol with a m.p. of 209°–211°.

In an analogous manner:

b) From (R)-1-[[10-chloro-4,6-dihydro-4-oxo-3-phenylpyrido[2,1-a]isoindol-1-yl]carbonyl]-2-(methoxymethyl)pyrrolidine there was obtained (R)-1-[[10-chloro-4,6-dihydro-4-oxo-3-phenylpyrido[2,1-a]isoindol-1-yl]carbonyl]-2-pyrrolidinemethanol with a m.p. of 158°–160° (acetonitrile).

c) From (R)-1-[[10-chloro-3-(m-chlorophenyl)-4,6-dihydro-4oxopyrido[2,1-a]isoindol-1-yl]carbonyl]-2-(methoxymethyl)pyrrolidine there was obtained (R)-1-[[10-chloro-3-(m-chlorophenyl)4,6-dihydro-4-oxopyrido[2,1-a]isoindol-1-yl]carbonyl]-2-pyrrolidinemethanol with a m.p. of 228°–230° (acetonitrile).

EXAMPLE 8 a) A mixture of 1.17 g of 1-[[2-(2-chloro-6-cyanophenyl)-1, 6-dihydro-6-oxo-5-phenyl-3-pyridyl]carbonyl]-3-methoxyazetidine, 0.91 g of zinc powder and 25 ml of acetic acid was heated to boiling under reflux for 15 minutes under argon. The reaction mixture was then poured into 125 ml of water, whereupon the separated crystals were filtered off under suction and washed with water. The aqueous phase was exhaustively extracted with methylene chloride. The combined organic phases were evaporated and the residue was purified with the crystals obtained above. This material was chromatographed on silica gel with methylene chloride/acetone (9:1) and then recrystallized from toluene. There was obtained 0.33 g of 1-[(10-chloro-4,6-dihydro-4-oxo-3-phenylpyrido[2,1-a]isoindol-1-yl)carbonyl]-3-methoxyazetidine as yellow crystals with a m.p. of 235°–238°.

In an analogous manner:

b) From 2-(2-chloro-6-cyanophenyl)-1,6-dihydro-N,N-dimethyl-6-oxo-5-phenylnicotinamide there was obtained 10-chloro-4, 6-dihydro-N,N-dimethyl-4-oxo-3-phenylpyrido[2,1-a]isoindole-1-carboxamide with a m.p. of 213°–216° (acetonitrile).

c) From 2-(2-chloro-6-cyanophenyl)- 1,6-dihydro-N,N-diethyl-6-oxo-5-phenylnicotinamide there was obtained 10-chloro-N,N-diethyl-4, 6-dihydro-4-oxo-3-phenylpyrido[2,1-a]isoindole-1-carboxamide with a m.p. of 180°–182° (ethyl acetate).

d) From 2-(2-chloro-6-cyanophenyl)-1,6-dihydro-N-(2-methoxyethyl)-6-oxo-5-phenylnicotinamide there was obtained 10-chloro-4,6-dihydro-N-(2-methoxyethyl)-4-oxo-3-phenylpyrido-[2,1-a]isoindole-1-carboxamide with a m.p. of 251°–257° (methanol).

e) From 1-[[2-(2-chloro-6-cyanophenyl)- 1,6-dihydro-6-oxo-5-phenyl-3-pyridyl]carbonyl]-4-methylpiperazine there was obtained after subsequent treatment with ethanolic hydrochloric acid 4-[[10-chloro-4,6-dihydro-4-oxo-3-phenylpyrido[2,1-a]isoindol-1-yl]carbonyl]-4-methylpiperazine hydrochloride with a m.p. of >300° (water).

f) From 2-(2-chloro-6-cyanophenyl)-N-ethyl-1, 6-dihydro-N(2-methoxyethyl)-6-oxo-5-phenylnicotinamide there was obtained 10-chloro-N-ethyl-N-(2-methoxyethyl)-4-oxo-3-phenylpyrido-[2,1-a]isoindole-1-carboxamide with a m.p. of 146°–148° (ethyl acetate).

g) From 1-[2-(2-chloro-6-cyanophenyl-5-(m-chlorophenyl)-1, 6-dihydro-6-oxo-nicotinoyl]-3-methoxyazetidine there was obtained 1-[[10-chloro-3-(m-chlorophenyl)-4,6-dihydro-4oxopyrido[2,1-a]isoindol-1-yl]carbonyl]-3-methoxyazetidine with a m.p. of 231°–234° (acetonitrile).

h) From (R)-1-[2-(2-chloro-6-cyanophenyl)-1, 6-dihydro-6-oxo-5-phenylnicotinoyl]-2-(methoxymethyl)pyrrolidine there was obtained (R)-1-[[10-chloro-4,6-dihydro-4-oxo-3-phenylpyrido-[2,1-a]isoindol-1-yl]carbonyl]-2-(methoxymethyl)pyrrolidine with a m.p. of 214°–216° (toluene).

i) From (R)-1-[2-(2-chloro-6-cyanophenyl)-5-(m-chlorophenyl)-1, 6-dihydro-6-oxo-nicotinoyl]-2-(methoxymethyl)pyrrolidine there was obtained (R)-1-[[10-chloro-3-(m-chlorophenyl)-4, 6-dihydro-4-oxopyrido[2,1-a]isoindol-1-yl]carbonyl]-2-(methoxymethyl)pyrrolidine with a m.p. of 136°–138° (ethyl acetate).

The compounds of formula V used as the starting material were prepared as follows:

A.a) A mixture of 72.9 g of methyl 11-chloro-4-oxo-3-phenyl4H-pyrido[2,1-a]phthalazine-1-carboxylate, 112 g of potassium hydroxide and 1,200 ml of methanol was heated to boiling under reflux for 46 hours under argon. The mixture was then concentrated to about 200 ml, the yellow suspension was diluted with 1,000 ml of water, filtered and the aqueous phase was extracted three times with 200 ml of methylene chloride each time. The aqueous phase was acidified with 25 percent hydrochloric acid and the separated crystals were filtered off, washed with water and dried in a vacuum. There was obtained 69.7 g of 2-[2-chloro-6-cyanophenyl)-1,6-dihydro-6-oxo-5-phenylnicotinic acid as yellowish crystals with a m.p. of 279°–281° (decomposition).

In an analogous manner:

A.b) From methyl 11-chloro-3-(m-chlorophenyl-4-oxo-4H-pyrido[2,1-a]phthalazine-1-carboxylate there was obtained 5-(m-chlorophenyl)-2-(2-chloro-6-cyanophenyl)-1, 6-dihydronicotinic acid with a m.p. of 308°–311° (decomposition; N,N-dimethylformamide/methanol).

B.a) A mixture of 1.4 g of 2-(2-chloro-6-cyanophenyl)-1,6-dihydro-6-oxo-5-phenylnicotinic acid, 40 ml of toluene and 0.1 ml of N,N-dimethylformamide was treated with 1.75 ml of thionyl chloride and stirred for 2 hours with the exclusion of moisture. The solvent was then removed in a vacuum and the residue was taken up in 40 ml of dioxane. After the addition of 1.7 ml of triethylamine the reaction mixture was treated with 0.38 g of 3-methoxyazetidine and stirred for 30 minutes. After concentration the residue was treated with 40 ml of water, whereupon the yellow crystals were filtered off and dried. There was obtained 1.17 g of 1-[[2-(2-chloro-6-cyanophenyl)-1, 6-dihydro-6-oxo-5-phenyl-3-pyridyl]carbonyl]-3-methoxyazetidine with a m.p. of 249°–253°.

In an analogous manner:

B.b) Using dimethylamine there was obtained 2-(2-chloro-6-cyanophenyl)-1, 6-dihydro-N,N-dimethyl-6-oxo-5-phenylnicotinamide with a m.p. of 264°–267° (ethyl acetate).

B.c) Using diethylamine there was obtained 2-(2-chloro-6-cyanophenyl)-1, 6-dihydro-N,N-diethyl-6-oxo-5-phenylnicotinamide with a m.p. of 237°–240° (acetonitrile).

B.d) Using 2-methoxyethylamine there was obtained 2-(2-chloro-6-cyanophenyl)-1, 6-dihydro-N-( 2-methoxyethyl)-6-oxo-5-phenylnicotinamide with a m.p. of 252°–255° (methanol/N,N-dimethylformamide).

B.e) Using N-methylpiperazine there was obtained 1-[[2-(2- chloro-6-cyanophenyl)-1, 6-dihydro-6-oxo-5-phenyl-3-pyridyl]carbonyl]-4-methylpiperazine with a m.p. of 250°–253° (methanol).

B.f) Using N-ethyl-N-(2-methoxyethyl)amine there was obtained 2-(2-chloro-6-cyanophenyl)-N-ethyl-1,6-dihydro-N-(2-methoxyethyl)-6-oxo-5-phenylnicotinamide with a m.p. of 184°–86° (ethyl acetate).

B.g) Using (R)-2-methoxymethyl)pyrrolidine there was obtained (R)-1-[2-(2-chloro-6-cyanophenyl)-1,6-dihydro-6-oxo-5-phenylnicotinoyl]-2-(methoxymethyl) pyrrolidine as a foam.

In an analogous manner, from 5-(m-chlorophenyl)-2-(2-chloro-6-cyanophenyl)-1, 6-dihydronicotinic acid:

B.h) Using 4-methoxyazetidine there was obtained 1-[2-(2-chloro-6-cyanophenyl)-5-(m-chlorophenyl)-1,6-dihydro-6-oxonicotinoyl]-3-methoxyazetidine with a m.p. of 239°–243° (acetonitrile).

B.i) Using (R)-2-(methoxymethyl)pyrrolidine there was obtained (R)-1-[2-(2-chloro-6-cyanophenyl)-5-(m-chlorophenyl)-1, 6-dihydro-6-oxo-nicotinoyl]-2-(methoxymethyl) pyrrolidine as a foam.

EXAMPLE 9

In analogy to Example 3.B, from 2.4 g of methyl 9-chloro-4, 6-dihydro-4-oxo-3-phenylpyrido[2,1-a]isoindole-1-carboxylate in the presence of 2.4 g of 10 percent palladium/carbon and a total of 3.6 g of ammonium formate there was obtained 1.68 g of methyl 4,6-dihydro-4-oxo-3-phenylpyrido[2,1-a]isoindole-1-carboxylate with a m.p. of 198°–202°.

The methyl 9-chloro-4,6-dihydro-4-oxo-3-phenylpyrido[2,1-a]isoindole-1-carboxylate used as the starting material was prepared as follows:

A. A solution of 151 g of triethyloxonium tetrafluoroborate in 3,200 ml of methylene chloride was stirred under argon at room temperature for 3.5 hours after the addition of 106.6 g of 6-chloro-2, 3-dihydro-1H-isoindol-1-one. The mixture was then treated within 40 minutes with 1.28 l of saturated sodium hydrogen carbonate solution, the organic phase was separated and washed with 1.28 l of water. After drying over sodium sulphate the organic phase was filtered and evaporated. The residue was taken up in 1.3 l of diethyl ether, whereupon it was stirred at room temperature for about 30 minutes. After removing insoluble material by filtration the filtrate was evaporated. There was obtained 110.5 g of 1-ethoxy-6-chloro-3H-isoindole with a m.p. of 64°–66°.

B. A suspension of 110.5 g of 1-ethoxy-6-chloro-3H-isoindole and 41.9 g of methylamine hydrochloride in 1,100 ml of ethanol was heated to boiling under reflux for 4 hours under argon, whereupon it was cooled to 2°, the separated crystals were filtered off under suction and recrystallized from ethanol. There are obtained 91.0g of 6-chloro-1-(methylimino)isoindoline hydrochloride as white crystals with a m.p. of >250°.

C. A mixture of 5.42 g of 6-chloro-1-(methylimino)isoindoline (prepared from the hydrochloride by treatment with 1.5 equivalents of 2N sodium hydroxide solution) and 120 ml of toluene was treated dropwise under argon at 0°–5° within 10 minutes with 5.96 g of α-carbonyl-phenylacetyl chloride. The mixture was stirred for 30 minutes, 4.47 g of 1,5-diazabicyclo[4.3.0]-non-5-ene in 30 ml of toluene were subsequently added dropwise thereto, the mixture was stirred at 0°–5° for a further 90 minutes, then treated with 50 ml of water and the separated crystals were filtered off under suction and washed with 35 ml of methylene chloride and, after drying, there was obtained 3.66 g of 9-chloro1, 2-dihydro-4-hydroxy-1-methyl-2-oxo-3-phenyl-6H-pyrimido[2,1-a]isoindol-5-ium hydroxide (internal salt) with a m.p. of 245° (decomposition). This product was recrystallized from N,N-dimethylformamide and then had a m.p. of 288°.

D. A mixture of 333 mg of 9-chloro-1,2-dihydro-4-hydroxy-1-methyl-2-oxo-3-phenyl-6 H-pyrimido[2,1-a]isoindol-5-ium hydroxide (internal salt) and 41 ml of toluene was treated with 0.86 g of methyl propiolate and heated to boiling under reflux for about 6.5 days, and 0.86 ml of methyl propiolate was added thereto every 24 hours. The reaction mixture was then cooled in an ice bath and the separated crystals were filtered off under suction. After recrystallization from N,N-dimethylformamide there was obtained 165 mg of methyl 9-chloro-4,6-dihydro-4-oxo-3-phenylpyrido[2,1-a]isoindole-1-carboxylate as yellowish crystals with a m.p. of 269°–273°.

EXAMPLE 10 a) A mixture of 1.04 g of methyl 2-(2-fluoro-6-cyanophenyl)1, 6-dihydro-6-oxo-5-phenylnicotinate, 0.98 g of zinc powder and 30 ml of acetic acid was heated to boiling under reflux for 30 minutes. The mixture was filtered while hot and the filtrate was evaporated in a vacuum. The residue was stirred overnight in 30 ml of water, whereupon the resulting crystals were filtered off under suction and washed with methylene chloride. By chromatography on silica gel with methylene chloride/diethyl ether (9:1) there was obtained yellow crystals which were recrystallized from ethyl acetate. There was obtained 0.23 g of methyl 10-fluoro-4,6-dihydro-4-oxo-3-phenylpyrido[2,1-a]isoindole-1-carboxylate with a m.p. of 134°–136°.

In an analogous manner:

b) From 1.09 g of methyl 2-(2-chloro-6-cyanophenyl)-1,6-dihydro-6-oxo-5-phenylnicotinate there was obtained 0.47 g of methyl 10-chloro-4,6-dihydro-4-oxo-3-phenylpyrido[2,1-a]isoindole-1-carboxylate with a m.p. of 172°–174° (ethyl acetate).

The compounds used as starting materials were prepared as follows in analogy to Example 4.A:

A. From 2.1 g of methyl 11-fluoro-4-oxo-3-phenyl-4H-pyrido[2,1-a]-phthalazine-1-carboxylate there was obtained with 4 equivalents of sodium methylate in methanol after chromatography on silica gel with methylene chloride/diethyl ether (9:1) and methylene chloride/acetone (9:1), 1.95 g of methyl 2-[2-fluoro-6-cyanophenyl)-1, 6-dihydro-6-oxo-5-phenylnicotinate as yellow crystals with a m.p. of 228°–233°.

B. From 5.5 g of methyl 11-chloro-4-oxo-3-phenyl-4H-pyrido[2,1-a]phthalazine-1-carboxylate there was obtained 5.2 g of methyl 2-(2-chloro-6-cyanophenyl)-1,6-dihydro-6-oxo-5-phenylnicotinate with a m.p. of 247°–250° (methanol).

EXAMPLE A

N,N-Dimethyl-4,6-dihydro-4-oxo-3-phenyl-pyrido[2,1-a]isoindole-1-carboxamide (compound A) was formulated by conventional means as the active ingredient into pharmaceutical preparations of the following compositions:

| a) Tablets | mg/tablet |
| --- | --- |
| Compound A | 5 |
| Lactose | 135 |
| Maize starch | 51 |
| Polyvinylpyrrolidone | 8 |
| Magnesium stearate | 1 |
| Table weight | 200 |
| b) Capsules | mg/capsule |
| Compound A | 10 |
| Lactose | 30 |
| Maize starch | 8.5 |
| Talc | 1 |
| Magnesium stearate | 0.5 |
| Capsule fill weight | 50 |

The compounds listed hereinafter can also be used in place of compound A as the active substance in the above compositions:

N,N-Dimethyl-4,6-dihydro-4-oxo-3-phenyl-pyrido[2,1-a]isoindole-1-carboxamide;

1-[(4,6-dihydro-4-oxo-3-phenylpyrido[2,1-a]isoindol-1-yl) carbonyl]-3-methoxyazetidine;

1-[(4,6-dihydro-6-oxo-7-phenylthieno[2',3':3,4]pyrrolo-[1,2-a]pyridin-9-yl )carbonyl]-3-methoxyazetidine;

(R)-1-[(4,6-dihydro-6-oxo-7-phenylthieno[2',3':3,4]pyrrol-[1,2-a]pyridin-9-yl)carbonyl]-2-(methoxymethyl)pyrrolidine;

(S)-1-[(4,6-dihydro-6-oxo-7-phenylthieno[2',3':3,4]pyrrolo-[1,2-a]pyridin-9-yl)carbonyl]-3-methoxypyrrolidine; and 1-[(10-chloro-4,6-dihydro-4-oxo-3-phenylpyrido[2,1-a]isoindol-1-yl) carbonyl]-3-methoxyazetidine.

We claim:

1. A compound of the formula

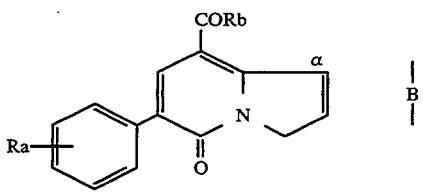

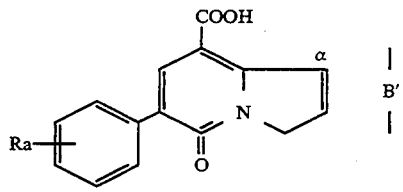

wherein Ra is hydrogen or halogen, Rb is —OR$^1$ or —NR$^2$R$^3$; R$^1$ is an unsubstituted lower alkyl or a lower alkyl substituted by hydroxy, lower alkoxy, amino, lower alkylamino, di(lower alkyl)amino, di(lower alkyl)carbamoyl or lower alkoxycarbonylamino; R$^2$ is hydrogen, an unsubstituted lower alkyl or a lower alkyl substituted by hydroxy, lower alkoxy, amino, lower alkylamino, di(lower alkyl)amino, di(lower alkyl)carbamoyl, or lower alkoxycarbonylamino; and R$^3$ is hydrogen or lower alkyl; B and the carbon atom denoted by α taken together is a group of the formula >Cα—CR$^4$=CH—CH=CH and R4 is hydrogen, fluorine or chlorine, or a pharmaceutically acceptable acid addition salt of the compound of formula I.

2. A compound according to claim 1, wherein Ra is hydrogen.

3. A compound according to claim 1, wherein Rb is —OR$^1$ and R$^1$ is lower alkyl.

4. A compound according to claim 1, wherein B and the carbon atom denoted by α taken together is a group of the formula >C$_α$—CH=CH—CH=CH— or >C$_α$—CCl=CH—CH=CH—.

5. A compound in accordance with claim 1, selected from N,N-dimethyl-4,6-dihydro-4-oxo-3-phenylpyrido[2,1-a]isoindole-1-carboxamide; N-ethyl-4,6-dihydro-N-(2-methoxyethyl)-4-oxo-3phenylpyrido[2,1-a]isoindole-1-carboxamide; N,N-diethyl-4,6-dihydro-4-oxo-3-phenylpyrido[2,1-a]isoindole-1-carboxamide; 4,6-dihydro-4-oxo-3-phenylpyrido[2,1-a]isoindole-1-carboxamide; N-(2-aminoethyl)-4,5-dihydro-4-oxo-3-phenylpyrido[2,1-a]isoindole-1-carboxamide; 10-chloro-4,6-dihydro-N,N-dimethyl-4-oxo-3-phenyl-pyrido[2,1-a]isoindole-1-carboxamide; 10-chloro-N,N-diethyl-4,6-dihydro-4-oxo-3-phenylpyrido[2,1-a]isoindole-1-carboxamide; 10-chloro-4,6-dihydro-N-(2-methoxyethyl)-4-oxo-3-phenylpyrido[2,1-a]isoindole-1-carboxamide; and 10-chloro-N-ethyl-N-(2-methoxyethyl)-4-oxo-3-phenylpyrido[2,1-a]isoindole-1-carboxamide.

6. A compound in accordance with claim 1, N-N-dimethyl-4,6-dihydro-4-oxo-3-phenylpyrido[2,1-a]isoindole-1-carboxamide.

7. A compound in accordance with claim 1, selected from methyl 4,6-dihydro-4-oxo-3-phenyl-4H-pyrido[2,1-a]isoindole-1-carboxylate; (dimethylcarbamoyl)methyl 4,6-dihydro-4-oxo-3-phenylpyrido-[2,1-a]isoindole-1-carboxylate; 2-(dimethylamino)ethyl-4,6-dihydro-4-oxo-3-phenylpyrido[ 2,1-a]isoindole-1-carboxylate; and methyl 10-fluoro-4, 6-dihydro-4-oxo-3-phenylpyrido[2,1-a]isoindole-1-carboxylate; and methyl 10-chloro-4,6-dihydro-4-oxo-3-phenylpyrido[2,1-a]isoindole-1-carboxylate.

8. A compound of the formula wherein B' and the carbon atom denoted by α taken together is a group of the formula >Cα—CH=CH—CH=CH— and Ra is hydrogen or halogen.

9. A compound of the formula:

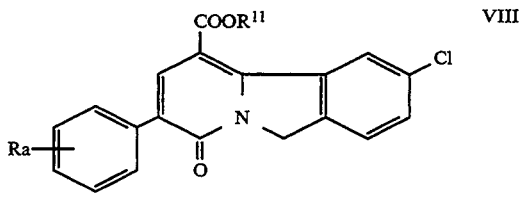

wherein R$^{11}$ is lower alkyl and Ra is hydrogen or halogen.

10. A pharmaceutical composition comprising a compound of the formula:

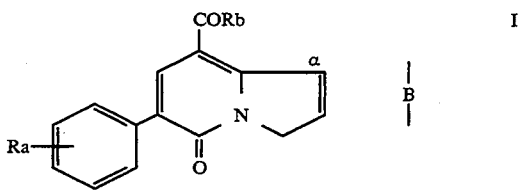

wherein Ra is hydrogen or halogen, Rb is —OR$^1$ or —NR$^2$R$^3$; R$_1$ is an unsubstituted lower alkyl or a lower alkyl substituted by hydroxy, lower alkoxy, amino, lower alkylamino, di(lower alkyl)amino, di(lower alkyl)carbamoyl or lower alkoxycarbonyl amino; R$_2$ is hydrogen, an unsubstituted lower alkyl or a lower alkyl substituted by hydroxy, lower alkoxy, amino, lower alkylamino, di(lower alkyl) amino, di(lower alkyl)carbamoyl or lower alkoxycarbonyl-amino; and R$^3$ is hydrogen or lower alkyl; B and the carbon atom denoted by α taken together is a group of the formula >Cα—CR$^4$=CH—CH=CH— and R$^4$ is hydrogen, fluorine or chlorine, or a pharmaceutically acceptable acid addition salt of the compound of formula I and an inert pharmaceutical carrier.

11. A pharmaceutical composition according to claim 10 wherein the compound is selected from N,N-dimethyl-4,6-dihydro-4-oxo-3-phenylpyrido[2,1-a]isoindole-1-carboxamide; N-ethyl-4,6-dihydro-N-(2-methoxyethyl)-4-oxo-3-phenylpyrido[2,1-a]isoindole-1-carboxamide; N,N-diethyl-4,6-dihydro-4-oxo-3-phenylpyrido[2,1-a]isoindole-1-carboxamide; 4,6-dihydro-4-oxo-3-phenylpyrido[2,1-a]isoindole-1-carboxamide; N-(2-aminoethyl)-4,5-dihydro-4-oxo-3-phenylpyrido[2,1-a]isoindole-1-carboxamide; 10-chloro-4,6-dihydro-N,N-dimethyl-4-oxo-3-phenylpyrido[2,1-a]isoindole-1-carboxamide; 10-chloro-N,N-diethyl-4, 6-dihydro-4-oxo-3-phenylpyrido[2,1a]isoindole-1-carboxamide; 10-chloro-4, 6-dihydro-N-(2-methoxyethyl)-4-oxo-3-phenylpyrido[2,1-a]isoindole-1-carboxamide; and 10-chloro- N-ethyl-N-(2-methoxyethyl)-4-oxo-3phenylpyrido[2,1-a]isoindole-1-carboxamide.

12. A pharmaceutical composition according to claim 10, wherein the compound is N-N-dimethyl-4,6-dihydro-4-oxo-3-phenylpyrido[2,1a]isoindole-1-carboxamide.

13. A pharmaceutical composition according to claim 10 wherein the compound is selected from methyl 4,6-dihydro-4-oxo-3-phenyl-4H-pyrido[2,1-a]isoindole-1-carboxylate; (dimethylcarbamoyl)methyl 4,6-dihydro-4-oxo-3-phenylpyrido-[2,1-a]isoindole-1-carboxylate; 2-(dimethylamino)ethyl-4, 6-dihydro-4-oxo-3-phenyl-pyrido[2,1-a]isoindole-1-carboxylate; and methyl 10-fluoro-4,6-dihydro-4-oxo-3phenylpyrido[2,1-a]isoindole-1-carboxylate; and methyl 10-chloro-4,6-dihydro-4-oxo-3-phenylpyrido[2,1-a]isoindole-1-carboxylate.

14. A method of controlling or treating muscle tension, stress, insomnia, anxiety or convulsions which comprises administering to a host requiring such controlling or treating, an effective amount of a compound of the formula:

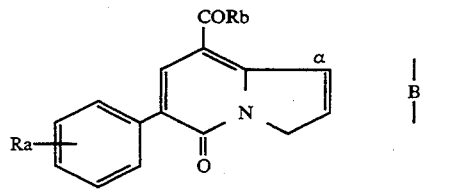

wherein Ra is hydrogen or halogen; Rb is OR$^1$ or NR$^2$R$^3$; R$^1$ is an unsubstituted lower alkyl or a lower alkyl substituted by hydroxy, lower alkoxy, amino, lower alkylamino, di(lower alkyl)amino, di(lower alkyl)carbamoyl or lower alkoxycarbonylamino; R$^2$ is hydrogen, an unsubstituted lower alkyl or a lower alkyl substituted by hydroxy, lower alkoxy, amino, lower alkylamino, di(lower alkyl)amino, di(lower alkyl)carbamoyl or lower alkoxycarbonylamino; R$^3$ is hydrogen or lower alkyl; B and the carbon atom denoted by α taken together is a group of the formula >Cα—CR$^4$=CH—CH=CH— and R$^4$ is hydrogen, fluorine or chlorine, or a pharmaceutically acceptable acid addition salt of the compound of formula I.

15. A method according to claim 14 wherein the compound is selected from N,N-dimethyl-4,6-dihydro-4-oxo-3-phenylpyrido[2,1-a]isoindole-1-carboxamide; N-ethyl-4,6-dihydro-N-(2-methoxyethyl)-4-oxo-3-phenylpyrido[2,1-a]isoindole-1-carboxamide; N,N-diethyl-4,6-dihydro-4-oxo-3-phenylpyrido[2,1-a]isoindole-1-carboxamide; 4,6-dihydro-4-oxo-3-phenyl-pyrido[2,1-a]isoindole-1-carboxamide; N-(2-aminoethyl)-4,5-dihydro-4-oxo-3-phenylpyrido[2,1-a]isoindole-1-carboxamide; 10-chloro-4,6-dihydro-N,N-dimethyl-4-oxo-3-phenylpyrido[2,1-a]isoindole-1-carboxamide; 10-chloro-N,N-diethyl-4,6-dihydro-4-oxo-3-phenylpyrido[2,1-a]isoindole-1-carboxamide; 10-chloro-4,6-dihydro-N-(2-methoxyethyl)-4-oxo-3-phenylpyrido[2,1-a]isoindole-1-carboxamide; and 10-chloro-N-ethyl-N-(2-methoxyethyl)-4-oxo-3-phenyl-pyrido[2,1-a]isoindole-1-carboxamide.

16. A method according to claim 14, wherein the compound is N-N-dimethyl-4,6-dihydro-4-oxo-3-phenylpyrido[2,1-a]isoindole-1-carboxamide.

17. A method according to claim 14 wherein the compound is selected from methyl 4,6-dihydro-4-oxo-3-phenyl-4H-pyrido[2,1-a]isoindole-1-carboxylate; (dimethylcarbamoyl)methyl 4,6-dihydro-4-oxo-3-phenyl-pyrido-[2,1-a]isoindole-1-carboxylate; 2-(dimethylamino)ethyl-4,6-dihydro-4-oxo-3-phenylpyrido[2,1-a]isoindole-1-carboxylate; and methyl 10-fluoro-4,6-dihydro-4-oxo-3-phenylpyrido[2,1-a]isoindole-1-carboxylate; and methyl 10-chloro-4, 6-dihydro-4-oxo-3-phenylpyrido[2,1-a]isoindole-1-carboxylate.

* * * * *

UNITED STATES PATENT AND TRADEMARK OFFICE
CERTIFICATE OF CORRECTION

PATENT NO. : 5,362,738

DATED : November 8, 1994

INVENTOR(S) : Serge Burner, Ulrich Widmer

Page 1 of 2

It is certified that error appears in the above-indentified patent and that said Letters Patent is hereby corrected as shown below:

Columns 23-25, claims 1, 10, and 14, delete

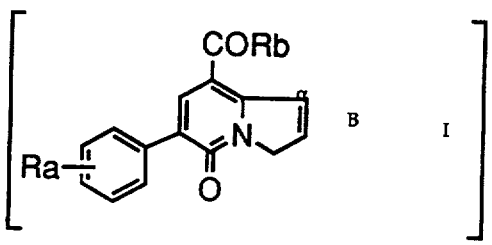 and add 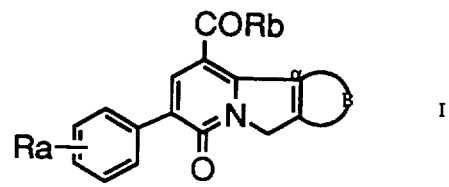

UNITED STATES PATENT AND TRADEMARK OFFICE
CERTIFICATE OF CORRECTION

PATENT NO. : 5,362,738                                        Page 2 of 2
DATED : November 8, 1994
INVENTOR(S) : Serge Burner, Ulrich Widmer It is certified that error appears in the above-indentified patent and that said Letters Patent is hereby corrected as shown below:

Column 24, delete

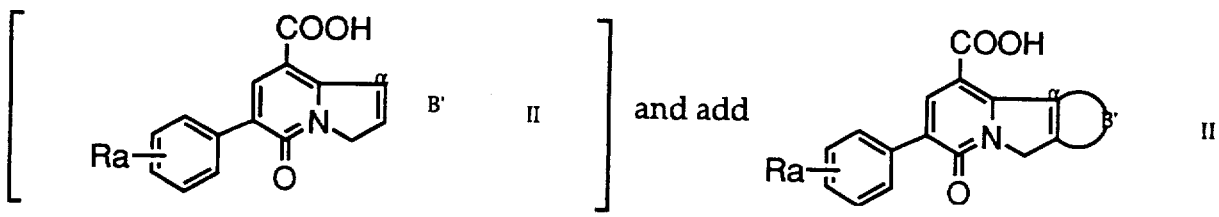

Signed and Sealed this

Twenty-third Day of May, 1995

Attest:

BRUCE LEHMAN

Attesting Officer             Commissioner of Patents and Trademarks